United States Patent [19]

Schmidt

[11] 4,198,341

[45] Apr. 15, 1980

[54] 2,5,5-TRIMETHYL-3-CARBALKOXY-4($\beta,\beta$-DIHALOVINYL)-4,5-DIHYDROFURANS

[75] Inventor: Hans-Georg Schmidt, Niederkassel, Fed. Rep. of Germany

[73] Assignee: Dynamit Nobel Aktiengesellschaft, Troisdorf, Fed. Rep. of Germany

[21] Appl. No.: 11,027

[22] Filed: Feb. 9, 1979

Related U.S. Application Data

[62] Division of Ser. No. 937,622, Aug. 28, 1978.

[30] Foreign Application Priority Data

Sep. 8, 1977 [DE] Fed. Rep. of Germany ....... 2740479
Mar. 23, 1978 [DE] Fed. Rep. of Germany ....... 2812672
Mar. 23, 1978 [DE] Fed. Rep. of Germany ....... 2812673
Jun. 9, 1978 [DE] Fed. Rep. of Germany ....... 2825363

[51] Int. Cl.$^2$ .......................................... C07D 307/32
[52] U.S. Cl. .................................................. 260/347.5
[58] Field of Search ................ 260/347.4, 347.5, 347.3

[56] References Cited

U.S. PATENT DOCUMENTS 3,919,261  11/1975  Merkle et al. .................... 260/347.5

Primary Examiner—Richard Raymond
Attorney, Agent, or Firm—Sprung, Felfe, Horn, Lynch & Kramer

[57] ABSTRACT

A method of preparing certain dihalogen vinyl cyclopropane carboxylic acid esters of the formula

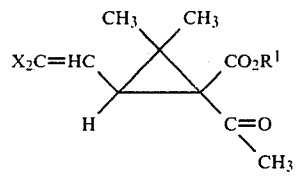

wherein R is an alkyl moiety and X is chlorine or bromine by exposing a dihalogen vinyl dihydrofuran of the formula

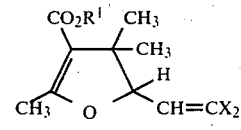

to light, e.g., ultraviolet light. Also disclosed is a method for preparing such 2,4,4-trimethyl-3-carbalkoxy-5-($\beta,\beta$-dihalogenvinyl)-4,5-dihydrofurans by reaction of a $\beta$-alkoxycrotonic acid ester or 3,3-bisalkoxybutyric acid ester with a 1,1,1-trihalogen-4-methyl-3- or -4-pentene-2-ol in the presence of an acid catalyst. Also disclosed is a method of converting such 2,4,4-trimethyl-3-carbalkoxy-5-($\beta,\beta$-dihalogenvinyl)-4,5-dihydrofuran by thermal rearrangement into 2,5,5-trimethyl-3-carbalkoxy-4-($\beta,\beta$-dihalogenvinyl)-4,5-dihydrofurans. Such 2,4,4- and 2,5,5-trimethyl-3-carbalkoxy-5-($\beta,\beta$-dihalogenvinyl)-4,5-dihydrofurans are new.

4 Claims, No Drawings

2,5,5-TRIMETHYL-3-CARBALKOXY-4($\beta$,$\beta$-DIHALOVINYL)-4,5-DIHYDROFURANS

This is a division of application Ser. No. 937,622, filed Aug. 28, 1978.

BACKGROUND

The subject of the invention is a method of preparing dihalogen vinylcyclopropanecarboxylic acid esters of the general formula

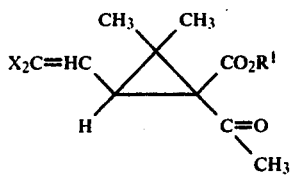

in which $R^1$ is a straight-chain or branched alkyl moiety and X represents chlorine or bromine.

The moiety $R^1$ is, for example, an alkyl moiety having 1 to 18, preferably 1 to 8 carbon atoms, especially 1 to 2 carbon atoms.

Known methods of preparing compounds of Formula I are described in German Offenlegungsschrift Nos. 2,606,635 and 2,649,856. Both methods set out from a 3,3-dimethylbutene-1 bifunctionalized in position 4, from which compounds of Formula I are obtained by adding on $CCl_4$, for example, and then cyclizing with bases. In both methods, staring materials are used which are difficult to obtain, so that the entire process is uneconomical and difficult.

THE INVENTION

It is the object of the present invention to provide a method for the preparation of cyclopropanes of General Formula I which will be generally applicable and economical on a commercial scale.

This object is achieved in accordance with the invention by transforming a dihalogen vinyl dihydrofuran of the general formula

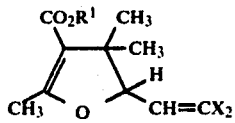

in which R1 and X have the same meaning as above, to compounds of Formula I by exposure to light.

The three-ring structure of Formula I, therefore, is obtained by a photochemical ring contraction of the correspondingly substituted dihydrofuran compound II.

It has surprisingly been found that very good yields can be achieved by the method of the invention. Contrary to expectations, only small amounts of undesired monomers and polymers are formed.

The ring contraction is performed with especially good yields by exposure to light having a wavelength greater than 200 nm. Especially suitable wavelength ranges are between 200 and about 400 nm, preferably between 230 and 300 nm.

The light source is preferably an ultraviolet lamp. However, any other light source which produces ultraviolet light or light containing ultraviolet can be used.

The reaction can be performed in the liquid phase, exposing, for example, the compound of Formula II as it is.

It is preferably to operate in the presence of an inert solvent, using solvents which are transparent to the radiation and do not enter into any reaction with the compounds of Formula I or of Formula II. Examples of suitable solvents are acetonitrile, alcohols, especially low aliphatic alcohols, diethyl ether, dioxane and the like, individually or in mixtures. Preferred as solvents are the low aliphatic alcohols, preferably methanol or ethanol.

The irradiation can be performed either by means of a lamp immersed in the liquid to be treated or by means of a source or several sources disposed on the outside of a reactor transparent to the radiation. Another variant consists in circulating the solution through the light exposure zone in a thin layer, such as a film for example, by means of circulation pumps. The liquid can also be subjected to illumination in the form of fine droplets, e.g., in the form of an emulsion or by the use of a spraying means. It is desirable to use inert gases, such as nitrogen and/or noble gases as the spraying aid.

In many cases, it is desirable to perform the irradiation in the absence of oxygen or gases containing oxygen. Inert gases of the above-described kind can be used for purging the liquid being exposed as well as the reactors, and as a shielding gas during the exposure.

If a submerged lamp is used or if the exposure of a liquid contained in a reactor is performed by means of a light source such as a lamp, for example, disposed outside of the reactor, it is desirable to keep the liquid in constant movement, by means, for example, of a stirrer or by means of an inert gas introduced into the liquid.

The ratio of admixture of the compounds of Formula II with the solvent can vary widely. Preferentially, 5x molar to 0.001x molar solutions are used for the irradiation.

The irradiation can also be performed in the gaseous phase, e.g., by means of a submerged lamp or a light source outside of the reactor, it being desirable to irradiate the gaseous starting product of Formula II, which can be mixed if desired with a gaseous solvent of the above-described kind, with the exclusion of gases containing oxygen, if desired. It is expedient to operate in the presence of an inert gas, such as nitrogen, and/or noble gases such as argon or helium.

Basically, one can also operate in the solid phase, although irradiation in the liquid phase or gaseous phase is preferred for commercial reasons.

The irradiation of the invention can be performed over a very broad range of temperatures. When operating in the liquid phase and gaseous phase, the limits are defined by the phase transformation points of the liquid or gas. The upper temperature limit is determined by the amount of thermal stress which the compounds of Formulas I and II as well as any solvents used can withstand.

In general, the reaction takes place satisfactorily in a temperature range between −50° and +250° C. A preferred temperature range is between −20° and +150° C., preferably 0° C. to 100° C. Since the reaction takes place without change in volume, it is independent of pressure. It is simplest, therefore, to operate at standard pressure; nevertheless, elevated or reduced pressure can also be applied.

In the reaction in the gaseous phase, however, it is preferable to apply a vacuum for the purpose of converting the liquid to the gaseous phase.

The process of the invention can be performed continuously or discontinuously.

The light exposure time depends on the flux density of the light source and on the amount of starting product involved, among other things. The optimum time can be determined by analytic methods, e.g., by gas chromatography.

The 2,4,4-trimethyl-3-carbalkoxy-5-($\beta,\beta$-dihalogenvinyl)-4,5-di-hydrofurans of Formula II are new. They can be obtained by the reaction of at least one $\beta$-alkoxycrotonic acid ester of the general formula

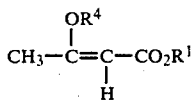

and/or at least one 3,3-bisalkoxybutyric acid ester of the general formula

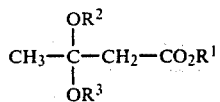

wherein $R^1$, $R^2$, $R^3$ and $R^4$ are alike or unalike, preferably alike, and are straight-chain or branched alkyl moieties, with (a) a trihalogen-4-methyl-3-pentene-2-ol of the general formula

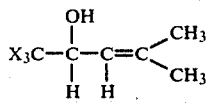

in which X represents chlorine or bromine atoms and/or with (b) a trihalogen-4-methyl-4-pentene-2-ol of the general formula

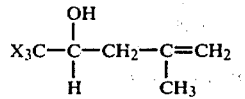

in which X represents chlorine atoms or bromine atoms, in the presence of an acid catalyst.

The moieties $R^1$, $R^2$, $R^3$ and $R^4$ are alkyl moieties of 1 to 18, preferably 1 to 8, and especially 1 or 2 carbon atoms.

Examples of suitable catalysts are Lewis acids, such as $AlCl_3$, $ZnCl_2$, $BF_3$, $FeCl_3$ and the like, protonic acids (Brönsted acids) such as $H_2SO_4$, $KHSO_4$, $KH_2PO_4$ $H_3PO_4$, p-toluenesulfonic acid, trichloroacetic acid, and acid ion exchangers. Mixtures of the individual acids can also be used.

The catalysts or catalyst mixtures are employed in amounts of up to 20 mole-%, preferably of less than 10 mole-%, with respect to the starting substance of General Formulas III and/or IV.

In the method of the invention for the preparation of the compounds of Formula II, hydrogen halide and an alcohol of the formula $R^2$—OH are liberated, provided that $R^3$ and, in some cases, $R^4$ are the same as $R^2$. If they are not, corresponding alcohol mixtures are liberated. Both products are preferably removed during the reaction.

The reaction is preferably performed at standard pressure, but in some cases with the application of a vacuum, for example for the distillative separation of a higher alcohol (higher-boiling alcohol) formed during the reaction, such as, for example, an alcohol having a boiling point higher than 160° C. at 760 mm Hg.

The compounds of Formula II and/or IV are reacted with the compounds of Formulas V and/or VI in a molar ratio of 1:0.5 to 1:10. Preferably, compounds V and/or VI are used in an excess. Preferably, the compounds of Formula III and/or IV are reacted with one of the compounds of Formulas V or VI, the radicals $R^1$, $R^2$, $R^3$ and $R^4$ being preferably alike.

The reaction is performed in a substantially waterfree medium. It is therefore desirable to use starting substances which are as dry as possible, and to conduct the reaction with the substantial exclusion of moisture.

The reaction can be performed in the presence of an inert solvent with the substantial exclusion of moisture. Inert solvents are, for example, those which do not render the starting product and the catalyst useless for the reaction and which do not react chemically with the end product. Suitable solvents are, for example, chlorobenzenes such as xylenes, dioxane, and dimethylformamide.

In general, amounts of solvents are used which will result, for example, in ratios of Compound III and/or IV to the solvent of from 2:1 to 1:10. Basically, however, the ratio can be greater than 2:1 or less than 1:10.

The reaction can, in principle, also be performed without the use of a solvent.

The reaction is performed at elevated temperature. In general, temperatures of 80° to 200° C. are employed, preferably 120° to 160° C.

Preferably the reaction is performed at the temperature at which the alcohol $R^2$—OH that forms or the alcohol mixture that forms can be separated by distillation at standard pressure or, in some cases, at reduced pressure, without doing thermal damage to the starting and end products.

The mixture should be stirred constantly during the reaction.

The process is generally performed in the following manner: The compounds of Formulas III and/or IV are heated with the trihalogen compounds of Formulas V and/or VI, with stirring, in the presence of the catalyst. The alcohol that forms is removed by distillation during the reaction. Preferably compounds III and/or IV are fed in portions or continuously to compounds V or VI or to a mixture of compounds V and VI. It is desirable that the feeding of these compounds be extended over the entire reaction time of, for example, 2 to 12 hours. After the reaction has ended, the mixture is worked up by fractional distillation in vacuo.

In the first fraction, one obtains the starting compound V and/or VI which was used in excess, and in the second fraction the dihydrofuran.

The compounds used in excess can be recycled without further purification after they have been separated by distillation.

For the preparation of the dihalogen vinyl cyclopropanocarboxylic acid ester of General Formula I, the reaction product which forms immediately when the bisalkoxybutyric acid ester and/or alkoxycrotonic acid ester is heated with at least one of the trihalogen compounds of Formulas V or VI while the alcohols that form are constantly removed by distillation, can be exposed to light in accordance with the invention, preferably after removal of the catalyst. Preferably, however, the reaction product is fractionally distilled to remove excess starting compounds before it is subjected to exposure in accordance with the invention. The same applies to the preparation of the 2,5,5-trimethyl-3-carbalkoxy-4-(β,βdihalogenvinyl)-4,5-dihydrofurans (VII) by the thermal rearrangement of 2,4,4-trimethyl-3-carbalkoxy-5-(β,β-dihalogenvinyl)-4,5-dihydrofurans (II).

The 3,3-bisalkoxybutyric acid alkyl esters (IV) are, for example, those obtainable by the method described on page 1199 of Beilstein, E III 3.

The β-alkoxycrotonic acid esters (III) can be prepared by reacting acetic acid ester with a mixture of alcohol and an orthoformate (A. Michael, G. H. Carlson, J. Amer. Chem. Soc. 57 (1935), page 162).

The trihalogen compounds of Formulas V and VI are obtainable by the reaction of isobutylene with trihalogen acetaldehydes (J. Colonge, A. Perrot, Comptes Rendues 239 (1954), page 541; E. J. Klimova, Chem. Abstr. 71 (1969 112335 K).

Additional subject matter of the invention are 2,5,5-trimethyl-3-carbalkoxy-4-(β,β-dihalogenvinyl)-4,5-dihydrofurans of the general formula

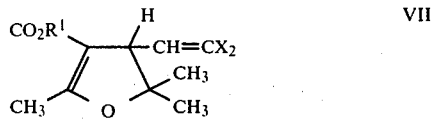

in which $R^1$ represents a straight-chain or branched alkyl radical and X represents Cl or Br, and a method of preparing dihydrofurans of Formula VII.

$R^1$ can be an alkyl moiety of 1 to 18 carbon atoms, preferably of 1 to 8 carbon atoms, and especially of 1 to 2 carbon atoms.

2,5,5-Trimethyl-3-carbalkoxy-4-(β,β-dihalogenvinyl)-4,5-dihydrofurans have not been known heretofore.

The 2,5,5-trimethyl-3-carbalkoxy-4-(β,β-dihalogenvinyl)-4,5-dihydrofurans are obtained by thermally rearranging 2,4,4-trimethyl-3-carbalkoxy-5-(β,β-dihalogenvinyl)-4,5-dihydrofurans of General Formula II

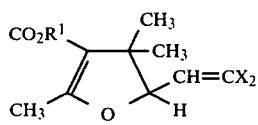

in which $R^1$ and X have the same meaning as above.

The thermolysis of the compounds of Formula II is best performed in the gaseous phase. If desired, a mixture of a compound of Formula II and an inert solvent can be subjected to thermolysis. It is recommendable to use those solvents which are in the gaseous state at the temperature of the thermolysis.

Fundamentally, the thermolysis can also be performed in the liquid phase, in the presence, if desired, of an inert solvent.

Suitable solvents are aromatic hydrocarbons such as, for example, benzene, or halogenated hydrocarbons such as carbon tetrachloride, for example.

The thermolysis temperature generally ranges between 200° and 500° C., although higher temperatures can be chosen if the time of thermolysis is shortened.

The molar ratio of admixture of solvents to compounds of Formula II can be varied widely. Good results are achieved, for example, by using approximately 1 to 1000 moles of the solvent or solvent mixtures per mole of the compound of Formula II. Larger amounts of solvent, however, can also be employed.

To facilitate the evaporation of the liquid or the thermolysis, as the case may be, the liquid is subjected to the heat treatment in the form of a thin layer or fine droplets.

For this purpose it is possible to use, for example, a temperature-controlled reaction tube in which the surface area is enlarged by the use of packing. The tube, in an upright position, for example, is provided at the top with an opening for the introduction of the starting product, and with a means for the introduction of an inert gas.

In the thermolysis, the procedure can be, for example, to feed the compound of Formula II, dissolved in a solvent if desired, drop by drop in liquid form, or to inject it in the form of a spray using an inert gas as the pressure and tranport medium. The compound to be thermolyzed, mixed, if desired, with an inert solvent, can also be introduced continuously or periodically in gas form into the actual thermolysis apparatus.

The rate of flow of the liquid or gas stream and hence the thermolysis time can be regulated on the basis of the dimensions of the reactor, the depth of fill, the dimensions and design of the packing, and the temperature of the reaction zone, by adjusting the required pressure gradient between the inlet and outlet openings of the tube and by the rate of feed. It is best to determine the optimum conditions by preliminary experiments.

After passing through the hot reaction zone the thermolyzate, which is in the form of a gas, let us say, is cooled to, for example, room temperature. The condensate is then subjected to a fractional distillation, preferably with the application of a vacuum.

The process of the invention is performed, for example, in a quartz reactor. Other reactor materials, however, are also suitable, such as ceramic material for example. Suitable packing bodies are, for example, bodies of quartz, or also of other materials such as ceramic.

The thermolysis can be performed at standard pressure or higher or lower pressure. Generally, it can be performed at a pressure of 0.1 Torr to 2 atmospheres.

It can be performed either continuously or discontinuously.

It is recommendable to assure the substantial exclusion of oxygen during the thermolysis, and for this reason it is desirable to purge the thermolysis apparatus prior to the thermolysis, with an inert gas, such as nitrogen, or with noble gases such as argon and/or helium. It is desirable that an inert gas be present also during the thermolysis.

The cyclopropanecarboxylic acid esters of General Formula I are a foreproduct of the acid component of synthetic pyrethroids, which have acquired industrial importance as insecticides of good persistence and low toxity to suckling animals (cf. M. Elliott, "Synthetic Pyrethroids," ACS Symposium, Series 42, American Chemical Society 1977). The active Insecticide can be synthezised as described in examples 1 and 13 of this invention.

The other new compounds of General Formulas II and VII are intermediates for the synthesis of insecticides. They can be transformed to compounds of formula I and further to the active insecticide.

EXAMPLES

The invention will be further explained with the aid of the following examples.

EXAMPLE 1

Four grams of 2,4,4-trimethyl-3-carbomethoxy-5-($\beta,\beta$-dichlorovinyl)-4,5-dihydrofuran are dissolved in 100 ml of acetonitrile and exposed at 0° C. to ultraviolet light of a wavelength longer than 200 nm produced by a submerged lamp. The time of exposure was one hour (lamp: Hanau Q 81, water-cooled medium-pressure mercury bulb). The reactor is a vertically disposed, temperature-controlled, cylindrical glass reactor having an inside diameter of 5.6 cm and a length of 20 cm. The bulb is housed in an immersion tube of quartz glass through which coolant (water) is circulated. The bulb and immersion tube are placed in the glass reactor so as to provide approximately 0.5 cm of annular clearance around them.

The contents of the reactor were purged with nitrogen for ten minutes before the illumination began, and during the illumination the liquid was kept in constant movement by the introduction of nitrogen.

The end point of the reaction was determined by gas chromatography.

After the exposure to light, the aoetonitrile is removed in vacuo and the residue is subjected to vacuum distillation. A uniform fraction was obtained at 99° to 102° C. (0.1 mm) (3.7 g=92.5% yield) which was identified as 1-acetyl-2,2-dimethyl-3-($\beta,\beta$-dichlorovinyl)-cyclopropanecarboxylic acid methyl ester (A).

MNR spectrum (100 MHz, CCl$_4$)$\delta$=5.80–6.00 (d d, 1 H); 3.75 (s, 3 H); 2.50–2.68 (d, d, 1 H); 2.20 (b s, 3 H); 1.14–1.24 (m, 6 H).

By the deacylation of A by the method described in German Offenlegungsschrift No. 2,649,856, the disclosure of which is hereby incorporated herein by reference, page 22, Example 17, a mixture of cis and trans isomers of 2,2-dimethyl-3-($\beta,\beta$-dichlorovinyl)-cyclopropanecarboxylic acid methyl ester is obtained, which is identical in its spectroscopic data with a sample of the genuine substance. This deacylation comprises: Analogues to example 17 (DE-OS No. 2,649,856) the methylester is treated with Na-methylate. The deacrylated methylester is isolated anologues to example 17 (DE-OS No. 2,649,856). Analogues to Fankas (Chem. L. sty 52688 (1958) the active insecticide can be synthesized (Methylester→acid→acid chloride→reaction with an alcohol e.g. allylmethylene (C.A. Vol. 52, U3650e). The higher allylesters can be treated in an analogues manner.

EXAMPLE 2

The same experimental arrangement was used as in Example 1.

5 g of 2,4,4-trimethyl-3-carbethoxy-5-($\beta,\beta$-dichlorovinyl)-4,5-dihydrofuran was dissolved in 100 ml of acetonitrile and irradiated at 20° C. with ultraviolet light of a wavelength greater than 200 nm. At the end of the irradiation the mixture was worked up as in Example 1. At 98° to 103° C. (0.05 mm), a uniform product passed over (4.7 g=94%), which was identified as 1-acetyl-2,2-dimethyl-3-($\beta,\beta$-dichlorovinyl)-cyclopropanecarboxylic acid ethyl ester. The structure was proven as in Example 1 by the NMR spectrum and by deacylation.

EXAMPLE 3

2,4,4-trimethyl-3-carbethoxy-5-($\beta,\beta$-dichlorovinyl)-4,5-dihydrofuran 242 g of 1,1,1-trichloro-4-methyl-3-pentene-2-ol was mixed with one gram of AlCl$_3$ and the mixture was heated at 145° C. With the exclusion of moisture, 109.5 g of $\beta$-ethoxycrotonic acid ethyl ester was added drop by drop with stirring over a period of 6 hours, while maintaining the temperature at 145° C. The low-boiling components were distilled out during the reaction. At the end of the reaction the mixture was worked up by fractional distillation. In the first fraction excess trichloro-4-methyl-3-pentene-2-ol is obtained. The dihydrofuran passes over in the second fraction (b.p.$_{0.1\ mm}$ 108°–109° C.), yield 177.4 g (91.7%). NMR spectrum (CCl$_4$, $\delta$): 1.05–1.20 (m, 9 H); 2.10 (s, 3 H); 4.0–4.30 (q, 2 H); 4.82 (d, 1 H); 5.97 (d, 1 H).

EXAMPLE 4

6.3 g of 1,1,1-trichloro-4-methyl-4-pentene-2-ol was mixed with 4.7 g of $\beta$-ethoxycrotonic acid ethyl ester and 0.1 g of AlCl$_3$ and the mixture is heated for 6 hours at 155° C., while the low-boiling components that formed were removed by distillation. The high-boiling components are fractionally distilled. 7.2 g is obtained (yield 86%) of 2,4,4-trimethyl-3-carbethoxy-5-($\beta,\beta$-dichlorovinyl)-4.5-dihydrofuran.

EXAMPLE 5

2,4,4-trimethyl-3-carbomethoxy-5-($\beta,\beta$-dichlorovinyl)-4,5-dihydrofuran 10.0 g of 1,1,1-trichloro-4-methyl-3-pentene-2-ol was mixed with 0.2 g of AlCl$_3$ and heated at 150° C. With the exclusion of moisture, 3.6 g of $\beta$-methoxycrotonic acid methyl ester was added drop by drop, with stirring, over a period of 4 hours, while maintaining the temperature at 150° C. The low-boiling substances that formed were removed by distillation. At the end of the reaction, the mixture was fractionally distilled. 6.6 g (yield 90.2%) of dihydrofuran was obtained (b.p.$_{0.1\ mm}$ 102°–104° C.). NMR spectrum (CCl$_4$, $\delta$): 1.14 (s, 3 H); 1.24 (s, 3 H); 2.15 (s, 3 H); 3.68 (s, 3 H); 4.85 (d, 1 H); 6.0 (d, 1 H).

EXAMPLE 6

2,4,4-trimethyl-3-carbethoxy-5-($\beta,\beta$-dibromovinyl)-4,5-dihydrofuran 12 g of 1,1,1-tribromo-4-methyl-3-pentene-2-ol was mixed with 0.1 g of KHSO$_4$ and 3.16 g of $\beta$-ethoxycrotonic acid ethyl ester and heated, with stirring for 12 hours at 145° C. while the low-boiling components that formed were removed by distillation. By fractional distillation of the mixture 6.0 g was obtained (yield 81%) of dihydrofuran (b.p.$_{2.5\ mm}$=120° C.). NMR spectrum (CCl$_4$, $\delta$): 1.10–1.40 (m, 9 H); 2.14 (s, 3 H); 4.0–4.30 (q, 2 H); 4.76 (d, 1 H); 6.50 (d, 1 H).

EXAMPLE 7

10 g of 2,4,4-trimethyl-3-carbomethoxy-5-($\beta,\beta$-dichlorovinyl)-4,5-dihydrofuran was dissolved in 200 g of benzene and this solution was passed, drop by drop, through an upright quartz tube filled with quartz spheres of 0.4 cm diameter, in the presence of nitrogen. The quartz tube had a length of one meter and a diameter of 3.5 cm. The depth of fill, which corresponded to the heating zone, was 30 cm. In the meantime the quartz tube was heated externally such that an internal temperature of 350° C. was measured in the center of the heating zone). The dropping rate amounted to 40 grams of solution per hour. The gaseous thermolyzate emerging from the tube was captured in a receiver and cooled to room temperature. After a fractional vacuum distillation of the condensate a uniform fraction is obtained (b.p.$_{1.0\ Torr}$: 91°–92° C.) in a yield of 7.9 g (=79%), which was identified by NMR spectroscopy and mass spectroscopy as 2,5,5-trimethyl-3-carbomethoxy-4-($\beta$,$\beta$-dichlorovinyl)-4,5-dihydrofuran.

NMR spectrum (100 MHz, CCl4); $\delta$=5.72 (d, 1 H); 3.72 (dq, 1 H); 3.65 (s, 3 H); 2.16 (d, 3 H); 1.41 (s, 3 H); 1.31 (s, 3 H).

EXAMPLE 8

10 g of 2,4,4-trimethyl-3-carboethoxy-5-($\beta$,$\beta$-dichlorovinyl)-4,5-dihydrofuran was thermolyzed as in Example 7. 7.3 g (=73%) of 2,5,5-trimethyl-3-carboethoxy-4-($\beta$,$\beta$-dichlorovinyl)-4,5-dihydrofuran (b.p. at 1.5 Torr: 102°–105° C. NMR spectrum (100 MHz, CDCl3): $\delta$=5.74 (d, 1 H); 4.14 (m, 2 H); 3.78 (bd, 1 H); 2.10 (bs, 3 H); 1.48–1.10 (m, 9 H).

EXAMPLE 9

2,4,4-Trimethyl-3-carbethoxy-5-($\beta$,$\beta$-dichlorovinyl)-4,5-dihydrofuran 6.1 g of 1,1,1-trichloro-4-methyl-3-pentene-2-ol was mixed with 0.1 g of AlCl3 and heated at 145° C. With the exclusion of moisture, 6.1 g of 3,3-bisethoxybutyric acid ethyl ester was added drop by drop, with stirring, over a period of 7 hours while maintaining the temperature at 145° C. The low-boiling components that formed were distilled out during the reaction. After the reaction had ended the mixture was worked up by fractional distillation. The dihydrofuran passed over at a boiling point of 108°–109° C. at a vacuum of 0.1 mm Hg. The yield is 6.7 g or 80%.

EXAMPLE 10

6.3 g of 1,1,1-trichloro-4-methyl-4-pentene-2-ol was mixed with 6.1 g of 3,3-bisethoxybutyric acid ethyl ester and 0.1 g of AlCl3 and the mixture was heated for 6 hours at 155° C., while the low-boiling components were removed by distillation. The high-boiling components were fractionally distilled. 6.9 g of 2,4,4-trimethyl-3-carbethoxy-5-($\beta$, $\beta$-dichlorovinyl)-4,5-dihydrofuran was obtained, the yield being 83%.

EXAMPLE 11

2,4,4-Trimethyl-3-carbomethoxy-5-($\beta$,$\beta$-dichlorovinyl)-4,5-dihydrofuran 6.1 g of 1,1,1-trichloro-4-methyl-3-pentene-2-ol was mixed with 0.2 g of AlCl3 and heated at 150° C. With the exclusion of moisture, 4.8 g of 3,3-bismethoxybutyric acid methyl ester was added drop by drop, with stirring, over a period of 4 hours while maintaining the temperature at 150° C. At the same time the low-boiling substance that formed were removed by distillation. After the reaction had ended the mixture was fractionally distilled. 6.6 g (yield 83%) of dihydrofuran was obtained having a boiling point of 102° to 104° C. at 0.1 mm Hg).

EXAMPLE 12

2,4,4-Trimethyl-3-carbethoxy-5-($\beta$,$\beta$-dibromovinyl)-4,5-dihydrofuran 10.5 g of 1,1,1-tribromo-4-methyl-3-pentene-2-ol was mixed with 0.1 g of KHSO4 and 6.1 g of 3,3-bisethoxybutyric acid ethyl ester and heated with stirring for 12 hours at 145° C., while the low-boiling components that formed were removed by distillation. By fractional distillation of the mixture, 7.7 g (yield 70%) of dihydrofuran was obtained having a boiling point of 120° C. at 2.5 mm Hg.

EXAMPLE 13

1-Acetyl-2,2-dimethyl-3-($\beta$,$\beta$-dibromvinyl)-cyclopnopane carboxylic acid-ethylester Anologues to example A one gram of 2,4,4-Trimethyl-3-carbalkoxy-5-($\beta$,$\beta$-dibromvinyl)-4,5 dihydrofuran is exposed to ultraviolet light. Purification of the photoproduct occured with thin layer chromolographic 0.6 g (60%) of the cyclopropane was obtained. NMR-spectrum (30 MHz, CCl4):$\delta$=6.30–6.80 (dd 1 H); 3.70–4.70 (m, 2 H); 2.35–2.80 (dd 1 H); 2.30 (n, 3 H); 1.0–1.6 (m, 9 H).

The active insecticide can be synthesized from this ethylester and the other low alkylesters as described in example 1 of this invention.

What is claimed is:

1. A 2,4,4-trimethyl-3-carbalkoxy-5-($\beta$,$\beta$-dihalogenvinyl)-4,5-di-hydrofuran of the formula

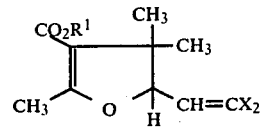

wherein $R^1$ is a straight-chain or branched alkyl radical and X represents chlorine or bromine.

2. A compound according to claim 1 wherein $R^1$ is a straight or branched alkyl radical of 1 to 8 carbon atoms.

3. A 2,5,5-trimethyl-3-carbalkoxy-4-($\beta$,$\beta$-dihalogenvinyl)-4,5-dihydrofuran of the formula

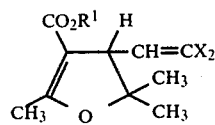

wherein $R^1$ is a straight-chain or a branched alkyl radical and X represents chlorine or bromine.

4. A dihydrofuran according to claim 3 wherein $R^1$ is a straight-chain or branched alkyl radical of 1 to 8 carbon atoms.

UNITED STATES PATENT AND TRADEMARK OFFICE
CERTIFICATE OF CORRECTION

PATENT NO. : 4,198,341
DATED : April 15, 1980
INVENTOR(S) : HANS-GEORG SCHMIDT

It is certified that error appears in the above-identified patent and that said Letters Patent are hereby corrected as shown below:

| Column | Line | |
|---|---|---|
| 4 | 9 | "II" should be --III--. |
| 7 | 31 | "aoetonitrile" should be --acetonitrile--. |
| 7 | 49 | "deacrylated" should be --deacylated--. |
| 10 | 20 | "cyclopno-" should be --cyclopro-" |

Signed and Sealed this

Nineteenth Day of August 1980

[SEAL]

Attest:

SIDNEY A. DIAMOND

Attesting Officer       Commissioner of Patents and Trademarks